(12) United States Patent
Hu et al.

(10) Patent No.: US 7,230,156 B2
(45) Date of Patent: Jun. 12, 2007

(54) METHOD FOR PREPARING A STERILE TRANSGENIC CARP

(75) Inventors: Wei Hu, Wuhan (CN); Zuoyan Zhu, Wuhan (CN); Yaping Wang, Wuhan (CN); Shuangfei Li, Wuhan (CN)

(73) Assignee: Institute of Hydrobiology, Chinese Academy of Sciences, Wuhan (CN)

( * ) Notice: Subject to any disclaimer, the term of this patent is extended or adjusted under 35 U.S.C. 154(b) by 0 days.

(21) Appl. No.: 11/094,286

(22) Filed: Mar. 31, 2005

(65) Prior Publication Data

US 2005/0257281 A1     Nov. 17, 2005

(51) Int. Cl.
*A01K 67/027* (2006.01)
*C12N 15/00* (2006.01)

(52) U.S. Cl. .......................... 800/25; 800/20
(58) Field of Classification Search .................. 800/20, 800/25
See application file for complete search history.

(56) References Cited

OTHER PUBLICATIONS

Ju et al, Developmental Genetics, 25: 158-167, 1999.*
Higashijima et al, Developmental Biology, 192: 289-299, 1997.*
Uzbekova et al, Journal of Molecular Endocrinology, 25: 337-350, 2000.*
Maclean et al, Gene, 295: 265-277, 2002.*
Wolf et al, J Pharm Pharmacol, Abstract, 1998.*
"Novel gene transfer into the fertilized eggs of gold fish" by Z. Zhu et al., Institute of Hydrobiology, Academia Sinica, Wuhan, P.R. China, pp. 31-34.
"A model of transgenic fish", Scientia Sinica B, Feb. 1989, pp. 147-155.
"Physiological and Pathological Analysis of the Mice Fed with "all-fish" Gene Transferred Yellow River Carp", by Z. Fuying et al., High Technology Letters 10: 17-19, pp. 511-513.
"Open a Door for Transgenic Fish to Market", by Z. Zuoyan et al., Biotechnology Information, 20001: 1-6.
"The formation of tetraploid stocks of red crucian carp x common carp hybrids as an effect of interspecific hybridization", by S. Liu, et al., Aquaculture 2001, 192(2-4): 171-186.

* cited by examiner

*Primary Examiner*—Deborah Crouch
*Assistant Examiner*—Magdalene Sgagias
(74) *Attorney, Agent, or Firm*—Birch, Stewart, Kolasch & Birch, LLP

(57) ABSTRACT

The present application disclosed a method for preparing a sterile transgenic fish, comprising constructing antisense RNA expression vector of salmon-type gonadotropin-releasing hormone, introducing the recombinant DNA fragment into carp oosperm by microinjection, and screening the sterile transgenic fish by Polymerase Chain Reaction and radioimmunoassay, wherein the expression vector comprising a promoter of carp beta actin (β-actin) gene, a complementary DNA fragment of antisense salmon-type gonadotropin-releasing hormone (sGnRH) gene from carp with 323 bp as a target gene comprising sGnRH decapeptide, the coding region of gonadotropin-releasing hormone associated peptide and 3' non-coding sequence, and 3' flanking sequence of grass carp growth hormone gene as a stop sequence. The method of the present invention is easy and convenient for operation which provides a basis for providing a technical platform of general applicability for solving the hereditary and ecological safety problems of transgenic fishes.

5 Claims, 4 Drawing Sheets

METHOD FOR PREPARING A STERILE TRANSGENIC CARP

TECHNICAL FIELD

The present invention relates to a field for transgenic fish. More specifically, the present invention relates to a method for preparing a sterile transgenic fish.

BACKGROUND

In 1984, the researchers in Institute of Hydrobiology, Chinese Academy of Sciences firstly developed the study concerning directive breeding in fishes by gene engineering in the world, and established an intact theory model for transgenic fishes and a perfect technique system for experiment (Zhu, Z., Li, G., He, L. and Chen, S. (1985)). Novel gene transfer into the fertilized eggs of goldfish (*Carassius auratus* L. 1758). Journal of Applied Ichthyology 1: 31–34. 2, Zhu, Z., Xu, K., Xie, Y, Li, G. and He, L. (1989). A model of transgenic fish. *Scientia Sinica* B (2): 147–155). On this basis, the study concerning the rapid growth of carp transformed with the "all-fish" growth hormone gene acquired important development. The test of large-scale breeding showed that the average weight of the offspring population of transgenic carp was 42% higher than that of the offspring population of the control fish, and that the available efficiency of bait increased 18.5% and that moreover comprehensively economic benefit of pond culture increased 125.7%. Meanwhile, the study concerning rapid growth of transgenic rainbow trout, Atlantic salmon and java tilapia and like in Europe and America also acquired important development, and the large-scale breeding tests thereof were also performed. However, hitherto, the commercial example of transgenic fishes has not been reported.

Indeed, as a directive-improved organism by genetic methods, the biological safety of transgenic fishes is concerned generally throughout the society. The biological safety of transgenic fishes comprises consumable safety of transgenic fish as food and genetic safety for releasing and ecological safety. Now, the study concerning transgenic fishes utilizes the gene component originated from fishes even themselves which eliminates the hidden danger of safety of transgenic fishes as food. Moreover, the test results for detecting the food safety of carps transformed with "all-fish" gene also showed that it is not remarkable influence for the growth, development and reproduction of the mouse after taking transgenic fishes (Zhang, F., Wang, Y., Hu, W., Cui, Z., Zhu, Z., Yang, J. and Peng, R. (2000) Physiological and pathological analysis of the mice fed with "all-fish" gene transferred Yellow River carp. High Technology Letters 10: 17–19). The establishment of high efficiency breeding model and the study results of food safety provide a basis for allowing the transgenic fishes commercial. Therefore, there is a need to solve the hereditary and ecological safety problems as well as the controlling technique thereof in the study of transgenic fishes, which is also a prerequisite for achieving the industrialization of transgenic fishes. The hereditary and ecological safety problems of transgenic fishes comprise two aspects generally: first, the Genebank contamination of natural species resources resulting from the possible crossing between transgenic fishes and wild species and close relative species; and second, the population structure of the ecosystem in the water would be destroyed which results in an irreversible influence if transgenic fishes form dominant population. However, on the one hand, the genetic shift of transformed genes by sexual mating can be controlled by preparing the sterile transgenic fishes, and on the other hand, the formation of dominant population of transgenic fishes escaping into the natural water system which further results in unadvantageous influence for the ecosystem in the water can be prevented by preparing the sterile transgenic fishes. Thereby, the hereditary and ecological safety of transgenic fishes can be solved by controlling the reproduction of transgenic fishes.

Now, the breeding for sterile transgenic fish utilizes triploid strategy, that is to say, crossing diploid transgenic fish with tetraploid fish to obtain sterile triploid transgenic fish (Zhu Z and Zeng Z, open a door for transgenic fish to market, Biotechnology Information, 2000, 1: 1–6). However, it is very difficult to obtain tetraploid. The allotetraploid crucian-carp obtained by Chinese researchers without chemical or physical treatment is only tetraploid fish with stable hereditary characters in the world that can reproduce by itself (Liu S, Liu Y, Zhou G et al, The formation of tetraploid stocks of red crucian carp×common carp hybrids as an effect of interspecific hybridization. Aquaculture, 2001, 192(2–4): 171–186). Therefore, the use triploid strategy for breeding sterile transgenic fishes is restricted to a great extent, and said strategy is only a specific example for solving the hereditary and ecological safety of transgenic fish and thereby does not possess generality.

DISCLOSURE OF THE INVENTION

The object of the present invention is to provide a method for preparing sterile transgenic fish, which is easy and convenient for operation, and to provide a technical platform having general availability for solving the hereditary and ecological safety problems of transgenic fish. The mechanism of the method utilizes antisense transgenic technique to block the expression of the gene concerned in the development of gonad and sexual mature of carp, salmon-type gonadotropin-releasing hormone gene (sGnRH gene), thereby block the reproductive function of transgenic fish and finally to obtain sterile transgenic fish.

For the above purpose, the present invention adopts the following technical steps to obtain sterile transgenic fish: constructing antisense RNA expression vector based on the mechanism of antisense nucleic acid technique and blocking the expression of salmon-type gonadotropin-releasing hormone gene.

The method of the present invention comprises: 1) constructing antisense RNA expression vector of salmon-type gonadotropin-releasing hormone gene; 2) preparing transgenic fish; and 3) screening sterile transgenic fish. Specifically, A: the promoter of carp β-actin gene (the nucleotide sequence thereof is represented by SEQ ID NO:1) is used as a promoter, a 323 bp cDNA fragment comprising antisense salmon-type gonadotropin-releasing hormone gene (sGnRH) from carp is used as a target gene (the nucleotide sequence thereof is represented by SEQ ID NO:2), which comprises specifically the coding region of sGnRH decapeptide, a gonadotropin-releasing hormone associated peptide (GAP) and 3' non-coding sequence, and 3' flanking sequence of grass carp growth hormone gene is used as a stop sequence (the nucleotide sequence thereof is represented by SEQ ID NO:3). After being digested by restriction endonuclease Nco I, Hind III and EcoR I, above three fragments are ligated with plasmid vector pUC118 to construct antisense RNA expression vector comprising recombinant gene CAsGnRHpc-antisense, pCAsGnRHpc-antisense (the nucleotide sequence thereof is represented by SEQ ID NO:4). B: Above antisense RNA expression vector pCAsGnRHpc-antisense is digested by restriction endonucleases Hind III and EcoR I to obtain the recombinant gene CAsGnRHpc-antisense, and then the recombinant gene is introduced into the carp oosperm. C: positive fish transformed with the recombinant gene is selected by PCR, and the sterile transgenic fish is selected by radioimmunoassay.

The present invention has following advantage and effects over the prior art: providing a new technical platform for preparing sterile transgenic fish which can be used to obtain sterile transgenic fish directly without breeding tetraploid fish; the frequency of sterile transgenic fish is about 32%; the method is easy and convenient for operation without the disadvantage resulting from breeding tetraploid fish and has general availability, and therefore can be used for breeding the sterile transgenic fish broadly; therefore, the method provides a basis for providing technical platform having general availability to solve the hereditary and ecological safety problems of transgenic fish thoroughly.

DESCRIPTION OF DRAWINGS

FIG. 1 is a schematic drawing of antisense RNA expression vector (pCAsGnRHpc-antisense) of salmon-type gonadotropin-releasing hormone gene from carp, wherein:

Number 1 represents the promoter of carp β-actin gene with 2532 bp length;

Number 2 represents a cDNA fragment of salmon-type gonadotropin-releasing hormone gene from carp with 323 bp length comprising the coding region of sGnRH decapeptide, gonadotropin-releasing hormone associated peptide (GAP) and 3' non-coding sequence;

Number 3 represents 3' flanking sequence of grass carp growth hormone gene with 790 bp length;

Number 4 represents plasmid vector pUC 118 with 3.2 kb length;

Number 5 represents restriction endonuclease Hind III site;

Number 6 represents restriction endonuclease EcoR I site;
Number 7 represents restriction endonuclease Nco I site;
Number 8 represents restriction endonuclease Cla I site;
Number 9 represents restriction endonuclease Pst I site.

Figure 1:
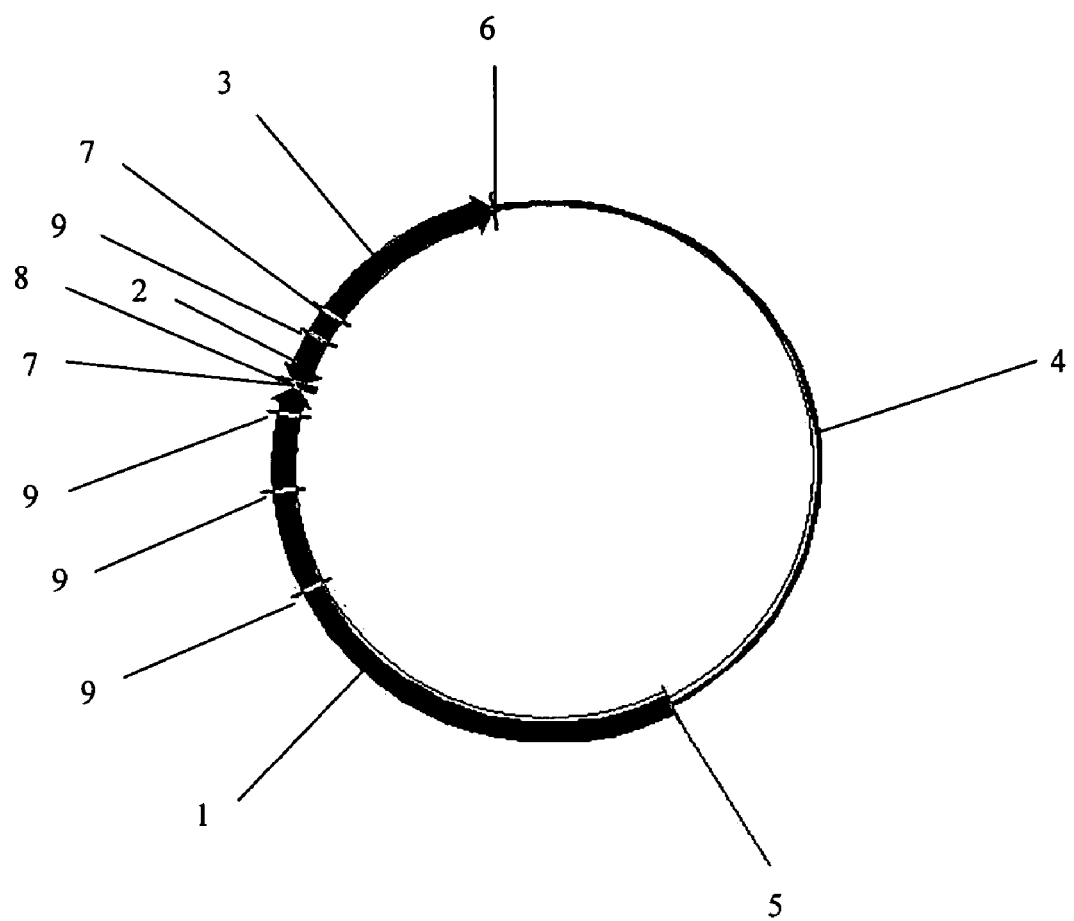
Figure 2:
Figure 2:

FIG. 2. Selection of pCAsGnRHpc-antisense positive clone, A: first selection for pCAsGnRHpc-antisense positive clone by PCR wherein the primer is Pnco-1+Pnco-2, the interest fragment is about 330 bp length, and M is the marker DL2000; B: Second selection for pCAsGnRHpc-antisense positive clone by PCR, wherein a, b and c represent the amplification results of first selected positive clone with the primers (P1+Pnco-2), (P1+Pnco-1) and (P1+P2), respectively, and the interest fragment is 830 bp, 0 bp and 800 bp length respectively, wherein M is the marker DL2000.

Figure 3:
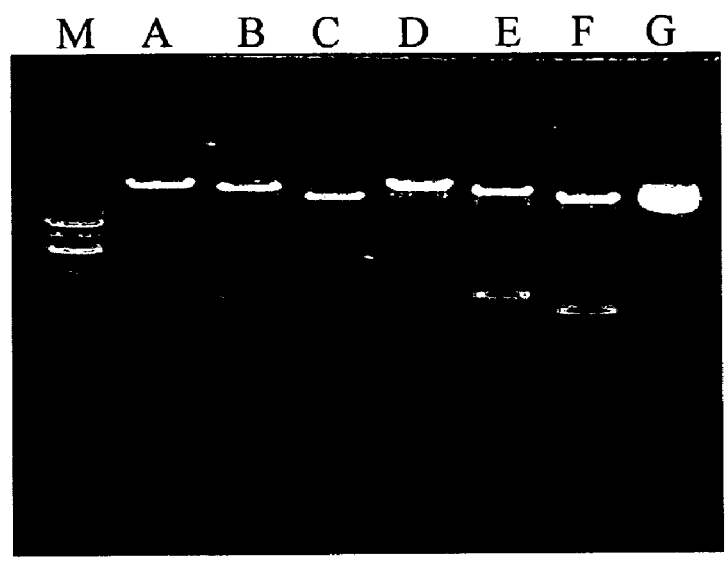

FIG. 3 is an electrophoresis map of plasmid pCAsGn-RHpc-antisense digested by restriction endonuclease, wherein A and D represent digestion by Nco I; B and E represent digestion by Cla I and EcoR I; C and F represent digestion by Pst I and EcoR I; G represents control plasmid; M represents the marker of 1 Kb ladder; and the group of A, B and C as well as the group of D, E and F represent digestion results of two different recombinants, respectively.

Figure 4:
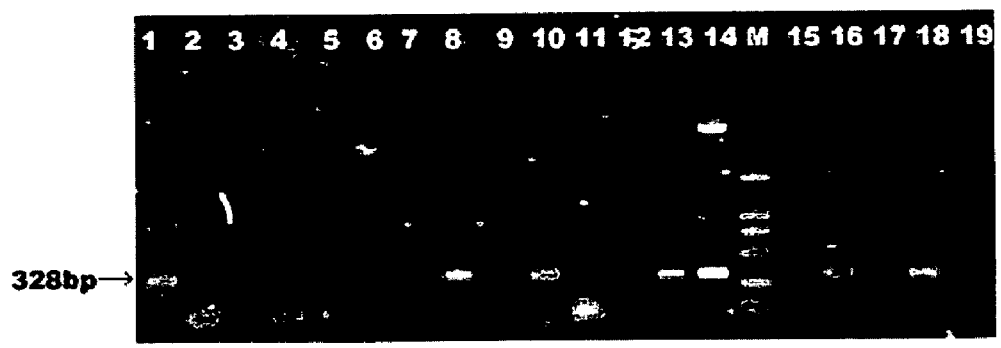

FIG. 4 is an electrophoresis map of transgenic fish by PCR detection, wherein lanes 1–19 represent numbered samples respectively and lane M is the marker DL2000.

Figure 5:
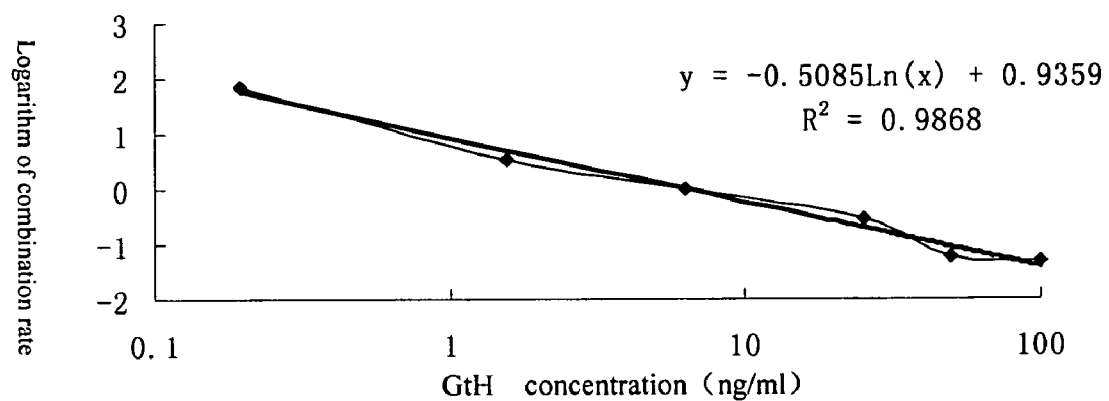

FIG. 5 represents a standard curve of carp type-II gonadotropin-releasing hormone (cGTH-II), wherein abscissa values have been logarithmically transformed.

Figure 6:
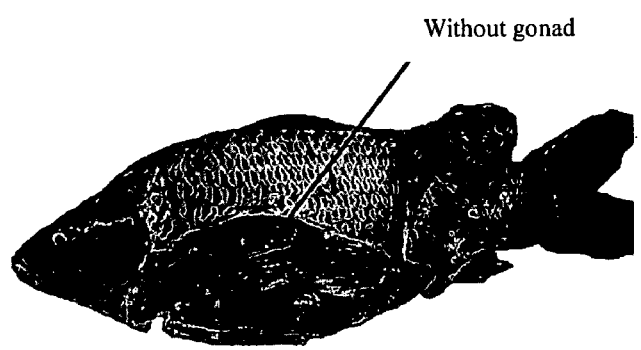

FIG. 6 is a picture of transgenic fish whose gonad development has been completely inhibited.

BEST MODE TO CARRY OUT THE PRESENT INVENTION

The present invention will be described in detail by the following examples. Those skilled in the art will understand that the following examples are used to illustrate the present invention, but are not to be construed to limit the present invention.

EXAMPLE 1

The Construction of Antisense RNA Expression Vector of Salmon-Type Gonadotropin-Releasing Hormone (pCAsGnRHpc-Antisense)

The antisense RNA expression vector of salmon-type gonadotropin-releasing hormone (pCAsGnRHpc-antisense) comprises a promoter of carp β-actin gene with 2532 bp length (the nucleotide sequence thereof is represented by SEQ ID NO:1 and which is obtained by selecting the genome library of carp by general methods), a 323 bp target gene which is the cDNA fragment of reversed salmon-type gonadotropin-releasing hormone gene from carp (the nucleotide sequence thereof is represented by SEQ ID NO:2) and is inserted into the downstream of the promoter by 3'–5' direction, a stop sequence of 3' flanking sequence of grass carp growth hormone gene with 790 bp (the nucleotide sequence thereof is represented by SEQ ID NO:3). The backbone of the antisense vector is pUC118 (SABC Corp.)

(1) The Specific Construction Process is as Follows.

The cDNA fragment of sGnRH (SEQ ID NO:2) is amplified by PCR with a template of sGnRH cDNA fragment (SEQ ID NO:2) and specific primers Pnoc-1 (5'-CGTC-CATGGCGTATCGATGTCGAC-3' SEQ ID NO:5) and Pnoc-2 (5'-AGCCCATGGCTTTGCCAGCATTGG-3', SEQ ID NO:6). The site of restriction endonuclease Nco I is designed in the 5'-end of primers of Pnco-1 and Pnco-2. The PCR program is performed by denaturing at 94° C. for 2 mins, then 32 cycles, each consisting of 94° C. for 30 seconds, 57° C. for 30 seconds and 72° C. for 40 seconds, and finally extending at 72° C. for 5 mins. Then, the above fragment is digested by Nco I completely. The plasmid pUC118 is digested by Hind III and EcoR I completely, and the promoter of carp β-actin gene is digested by Hind III and Nco I completely and the 3' non-coding region of grass carp growth hormone gene is digested by Nco I and EcoR I completely. Then, the above fragments are ligated by T4 ligase (Takara Corp.) for 4 hours at 16° C.

E. coli (strain E. coli TOP10 and Top 10F': Invitrogen Corp., and E. coli TOP 10 gentype is F-mcrAΔ(mrr-hs-dRMS-mcrBC) φ80lacZΔM15Δ/acX74 deoR recA1 araD139Δ(ara-leu)7697 galu galk rpsL (StrR) endA1 nupG) is transformed with the above ligation product and is cultured at 37° C. The single colony is selected and inoculated into LB liquid medium to identify.

Above PCR reaction, digestion reaction, ligation reaction, DNA transformation, bacterial culture as well as the used medium refer to the description of Molecular cloning, a laboratory manual $2^{nd}$ ed. Cold Spring Harbor Laboratory press, 1989. J. Sambrook, et al.

(2) The Identification of Antisense RNA Expression Vector (pCAsGnRHpc-antisense)

(i) PCR Identification

The identification of antisense RNA expression vector is performed by two PCR reactions.

Firstly, PCR was performed in 25 μL system using 2 μL bacterial suspension cultured in liquid LB medium at 37° C.

for 5 hours as a templet and specific primers Pnoc-1 and Pnoc-2 to amply the interest fragment about 330 bp(FIG. 2-A).

Secondly, PCR was performed in 25 μL system using 2 μL bacterial suspension cultured in liquid LB medium at 37° C. for 5 hours as a templet and specific primer pairs P1 (5'-AAATGAATGGGCTGAGGATG-3', SEQ ID NO: 7, which is located on the promoter of β-actin and about 500 bp of the upstream of the antisense sGnRH cDNA fragment) +Pnco-2, P1+Pnoc-1 and P1+P2 (5'-TGGCTTCCTGGTG-GAAAGA-3', SEQ ID NO: 8, which is located on the inside of Pnoc-2 upstream) to amply the interest fragments about 830 bp, 0 bp and 800 bp, respectively.

Above PCR reactions belong to general PCR reactions and are performed by denaturing at 94° C. for 2 mins, then 32 cycles of 94° C. for 30 seconds, 57° C. for 30 seconds and 72° C. for 40 seconds, and finally extending at 72° C. for 5 mins.

(ii) Digestion Identification

The positive colony identified by above reactions is used to prepare plasmids according to general methods (Molecular cloning, a laboratory manual 2nd ed. Cold spring harbor laboratory press, 1989. J. Sambrook, et al) and the plasmid DNA extract was digested with one of restriction endonuclease Nco I, Cla I, EcoR I and Pst I or both of them for further identification. (the result is in FIG. 3)

(iii) Sequencing Identification

The confirmed plasmid was sequenced by specific primer (5'-TGGCGTGATGAATGTCG-3', SEQ ID NO: 9) (Sangon Corp.) to prove the accuracy of the constructed vector which has the nucleotide sequence represented by SEQ ID NO:4.

EXAMPLE 2

The Preparation of a Transgenic Fish

The antisense RNA expression vector of salmon-type gonadotropin-releasing hormone (pCAsGnRHpc-antisense) is digested by restriction endonuclease EcoR I and Hind III to obtain linear recombinant DNA fragment (CAsGnRHpc-antisense). The recovered DNA fragment was dissolved into buffer ST (88 mM NaCl, 10 mM Tris-HCl, pH7.5) with a final concentration of 50 ng/μL. The oosperm of carp is digested by 0.25% trypsase to remove ootypus and then is introduced with above DNA solution at animal pole before first merogenesis by microinjection method. And the amount of DNA is about 5×10⁵ copies/oosperm. The oosperm treated by micromanipulation is then incubated in sterile environment of the laboratory.

EXAMPLE 3

The Selection of the Sterile Transgenic Fish (1) The Detection of Positive Transgenic Fish by PCR The DNA fragment was extracted from tail fin tissue of carp with 0.5×0.5 cm size. The tube containing tail fin of carp was added 0.4 ml DNA extraction buffer (10 mmol/L EDTA, 10 mmol/L Tris HCl, 300 mmol/L NaCl, 2% SDS) and then incubated in water bath at 55° C. for 1–2 hours followed by incubating in water bath at 37° C. overnight. The digested tissue solution was extracted by phenol, phenol/chloroform, and chloroform, respectively and was precipitated by adding 2.5 fold volume of ethanol. Once performed, the precipitate was transferred into another tube on time and was washed by 70% ethanol, and then precipitated by centrifuging with high speed for 1 min. Ethanol was removed from the tube completely and then the tube was incubated in the incubator at 37° C. for 15 min. Suitable volume of TE buffer containing 20 mg/ml RNase was added into the tube and then the tube was placed in the incubator at 37° C. for 2 hours.

PCR was performed with forward primer (5'-CCATG-GCGTATCGATGTCGAC-3', SEQ ID NO: 10) located on the linker sequence between the promoter and the reverse targeted sequence and backward primer (5'-CATG-GCTTTGCCAGCATTGG-3', SEQ ID NO:11) located on the targeted sequence in GeneAmp PCR system 9600 (Perkin Elmer) by denaturing at 94° C. for 2 mins, then 32 cycles of 94° C. for 30 seconds, 57° C. for 30 seconds and 72° C. for 40 seconds, and finally extending at 72° C. for 5 mins. The amplified fragment is about 330 bp. (See FIG. 4).

(2) The Identification of Male Carp

The blood sample was taken from tail vascular of positive transgenic fish and the concentration of 11-ketotestosterone in the serum of positive transgenic fish was detected to identify male carp according to the method described on the kit (11-ketotestosterone EIA test kit, Biosense laboratories).

(3) The Detection of the Content of Gonadotropin in the Serum and the Selection of Sterile Transgenic Fish About 0.4 ml blood sample was taken from tail vascular of the transgenic carp. After displacing at 4° C. for 3–4 hours, the serum was obtained by centrifuging and then stored at −70° C. 50 μL serum was used to perform radio-immunoassay (RIA) of gonadrotropin. The standard curve was established based on the different concentration of gonadrotropin and dilution factor by double-antibody radio-immunoassay according to the description of the reference (Peter, R. E., Nahorniak C S, Chang J. P. and Crim L. Gonadotropin release from the pars distalis of goldfish, *Carassius auratus*, transplanted beside the brain or into the brain ventricles: Aquaculture, 1984, 83: 193~199. Wang D, Lin H and H J Th Goos. Studies on the regulation of gonadotropin secretion in the bagrid catfish, *Mystus macropterus*. Acta Zoologica Sinica, 1998, 44(3): 322–328.) to determine the content of gonadotropin (GtH) in the serum of the transgenic fish (FIG. 5). If the content of gonadotropin in the serum of test fish is 60% lower than the content of gonadotropin in the serum of the positive transgenic fish of same batch, the sterile transgenic fish is identified, which can be further confirmed by dissection (FIG. 6).

The invention claimed is:

1. A method for preparing a sterile transgenic carp comprising:
   (i) constructing antisense RNA expression vector comprising a backbone vector, a carp β-actin gene promoter comprising SEQ ID NO: 1, a carp salmon-type gonadotropin-releasing hormone gene comprising a nucleotide sequence encoding SEQ ID NO: 2 and a 3'flanking sequence of grass carp growth hormone gene, comprising SEQ ID NO: 3, where the carp salmon-type gonadotropin-releasing hormone gene operably linked to the carp β-actin gene promoter in a 3'–5'direction;
   (ii) preparing a transgenic carp by injecting the antisense RNA expression vector into a carp embryo;
   (iii) screening resulting transgenic carp by Polymerase Chain Reaction to determine carp positive for the transgene and determining serum GtH concentration of positive carp by RIA;
   (iv) comparing the serum GtH concentration of positive carp; and
   (v) identifying sterile carp whose genome comprises the antisense RNA expression vector.

2. The method of claim 1, wherein the backbone vector is pUC118.

3. The method of claim 1, wherein said antisense RNA expression vector is pCAsGnRHpc-antisense as set forth in SEQ ID NO: 4.

4. The method of claim 1, wherein the carp is common carp (*Cyprinus carpio* L.).

5. The method of claim 1, wherein the sterile transgenic carp is obtained if the GtH concentration in the serum thereof is 60% lower than the average content of GtH in the serum of the positive transgenic carp of the same batch.

* * * * *

SEQUENCE LISTING

<160> NUMBER OF SEQ ID NOS: 11

<210> SEQ ID NO 1
<211> LENGTH: 2532

<212> TYPE: DNA
<213> ORGANISM: Carp

<400> SEQUENCE: 1

| | | | | | |
|---|---|---|---|---|---|
| aagcttttag | accttcttac | ttttggggat | tatataagta | ttttctcaat | aaatatctca | 60 |
| tatcttactg | tggtttaact | gctgaatcta | aaattttaat | acaaaagtag | ttatatttgt | 120 |
| tgtacattgt | aaactataac | ttaacttcag | tttcagagaa | actcatgtgc | tcaaaatgta | 180 |
| aaaaagtttt | cctgttaaat | attttgtaaa | tgtattgaag | acaaaataag | aaaaaaaaaa | 240 |
| tataagccac | taaatcacac | tgtccttggt | atcagcaaga | gattctgaca | taatcagctg | 300 |
| tttttgttta | ttactgccat | tgaaggccat | gtgcattagt | cccaagttac | acattaaaaa | 360 |
| gtcacatgta | gcttaccaac | atcagtgctg | ttcaagcaca | gcctcatcta | ctattcaaac | 420 |
| tgtggcacca | tctaaaatat | gccagaattt | ttttatttaa | tgaatttgac | cctgaaatat | 480 |
| gtattaatat | cactcctgtg | atttttttgt | aatcagctta | caattacagg | aatgcaagcc | 540 |
| tgattcatta | caagtttcac | tacactttct | ctgacaacat | cacctactga | actcagacca | 600 |
| gctagttgct | ccttaagtat | acaatcatgt | cactaatcct | catttcaatg | aaaaatacc | 660 |
| ctattgtact | tggtacttgg | tagataacca | cagagcagta | ttatgccatt | attgtgaata | 720 |
| caataagagg | taaatgacct | acagagctgc | tgctgctgtt | gtgttagatt | gtaaacacag | 780 |
| cacaggatca | aggaggtgtc | catcactatg | accaatacta | gcactttgca | caggctcttt | 840 |
| gaaaggctga | aaagagcctt | attggcgtta | tcacaacaaa | atacgcaaat | acggaaaaca | 900 |
| acgtattgaa | cttcgcaaac | aaaaaacagc | gattttgatg | aaaatcgctt | agggatcccc | 960 |
| ccttgctctt | caaacaatcc | agcttctcct | tctttcactc | tcaagttgca | agaagcaagt | 1020 |
| gtagcaatgt | gcacgcgaca | gccgggtgtg | tgacgctgga | ccaatcagag | cgcagagctc | 1080 |
| cgaaagttta | ccttttatgg | ctagagccgg | gcatctgccg | tcatataaaa | gagcgcgccc | 1140 |
| agcgtctcag | cctcactttg | agctcctcca | cacgcagcta | gtgcggaata | tcatctgcct | 1200 |
| gtaacccatt | ctctaaagtc | gacaaacccc | cccaaaccta | aggtgagttg | atctttaagc | 1260 |
| tagctttta | cattttcagc | tcgcatatat | caattcgaac | gtttaattag | aatgtttaaa | 1320 |
| taaagccaga | ttaaatgatt | aggctcagtt | accggtcttt | tttttctcat | ttacgtgcga | 1380 |
| actctgctta | aactctagtt | attctttatt | aatatgtggt | tatttttata | tatgtatgtg | 1440 |
| ttatcataac | tgtactggct | atgtcaggtg | gtaatgactg | taacgttacg | ttactcgttg | 1500 |
| taggcacgac | attgaatggg | ccggtgttga | ataagtctt | caacccctt | taacctcaaa | 1560 |
| atgtgctctg | gttaacaagg | attttaacag | ctatcagtat | gactgtgcgg | ttttaaagcc | 1620 |
| gttagtgagg | cacgttgcac | acttgatgga | tggccggaat | gggaagttct | ttatgcaggc | 1680 |
| agtgctgcag | cagggtgtga | cctactttag | ctaacgttag | ccggctaacc | agcattcatc | 1740 |
| tgccggtaac | ttgagtctaa | tattctctca | tgtgatatcg | aagtgatcaa | agacacgtct | 1800 |
| gttagctcac | tttaaccaac | tgtagtgaaa | aatagcgcag | tgtgcagccc | ttcagtcttt | 1860 |
| catttaggct | gattattcaa | tcatttattt | aactattaac | gcgttactaa | acgtaaggta | 1920 |
| acgtagtcag | tttttaataa | ctggtgaaaa | gtactggttg | ggtttaaatg | gtgacttata | 1980 |
| attgtgttgg | agggggaaac | cttttttgata | aaggctatat | aatctcaaat | gaatgggctg | 2040 |
| aggatggtgt | tcacaggtgc | tttagtgaag | tccgctcgtg | aagagtcgct | gaagtgactg | 2100 |
| cagatctgtg | acgcagtcgt | tttgggcaga | cggccgttga | aattcggttg | agtaattgat | 2160 |
| accaggtgag | gctagaggat | gtagaaattc | atttgtgtag | aatttaggga | gtggccctgg | 2220 |

```
cgtgatgaat gtcgaaatcc gttccttttt actgaaccct atgtctctgg ctgagtgcca    2280
caccgccggc agccgcaaag cgtctcaaac cattgccttt tatggtaata atgagaatgc    2340
agagggactt cctttgtctg gcacatctga ggcgcgcatt gtcacactag cacccactag    2400
cggtcagact gcagattgca gcacgaaaca ggaagctgac tccacatggt cacatgctca    2460
ctgaagtgtt gacttccctg acagctgtgc actttctaaa ccggttttct cattcattta    2520
cagttacagc ca                                                       2532

<210> SEQ ID NO 2
<211> LENGTH: 323
<212> TYPE: DNA
<213> ORGANISM: Carp

<400> SEQUENCE: 2
tggcgtatcg atgtcgactt ttttttttt ttttacatgg aataaaattt taatttattc      60
tcgttggcta cagggttta tcttcatcct ttatgctttt acactcttcc tcgtcttttg     120
ggaaatctca gttctttcag aggcaaacct tcagcatcca cttcattcac tatgtgtatc    180
ggtgaaagtt gttccattgg agagtctgca ggaatggata gtactgcatc accagcatcc    240
atcatcctaa atgttgcctc acttcacca acgcttctct ttccaccagg aagccaacca    300
tatgaccaat gctggcaaag cca                                           323

<210> SEQ ID NO 3
<211> LENGTH: 790
<212> TYPE: DNA
<213> ORGANISM: Grass Carp

<400> SEQUENCE: 3
tgggggagag cagcctcaga gagagctttc gtcttctggc ttgcttcaag aaggacatgc     60
acaaggtgga aacttacctg agggttgcga attgcaggag atccctggat tcaaactgca    120
ccctgtagat ggcgccaatg tattgctagc caaagcctgt gacacacttt gctgcaaatc    180
taaaaccagt ttaagtcctc aaaatctcct aatataatta ttatctggtc ttatatatgc    240
aggaaatgtc aaccaggcat ggctaggtct gttctctagt tccctcccat atctaaaccc    300
aacactattg tatttattct tctcattggg gagtgctcgt aaattaaaga cattaagatc    360
tgatttaaca tttcacagtg gtgctaagca atatatggca atatattttc aaatgtgccc    420
aaatcgcttt gactctagta ttttatggct ccaaaaatgg ctaaagatgc cttttgtcga    480
aactgtcatt tggatggatg ggttcactcc caaccaagtg tatgaatgta acatttgtc    540 tgtctgatag attatgtcca tattattagc tcatgctgtt ctcttgaagc tgtgtgtctt    600
tatccattaa atttctaaac tgcatccaat gtgtctgctg tatgacctgt gtggtttatt    660
tttttctacc cgtctcaaca ttacacgtac cttacatttt cactgctcgg atattcatca    720
aaatcagtcc tatcatccgt ccacaatgaa cgagttcaaa atggaccgaa aaaaatgacc    780
agcggaattc                                                          790

<210> SEQ ID NO 4
<211> LENGTH: 3645
<212> TYPE: DNA
<213> ORGANISM: Artificial Sequence
<220> FEATURE:
<223> OTHER INFORMATION: Description of Artificial Sequence: Synthetic
      anti-sense expression derived from Carp

<400> SEQUENCE: 4
```

| | |
|---|---|
| aagcttttag accttcttac ttttggggat tatataagta ttttctcaat aaatatctca | 60 |
| tatcttactg tggtttaact gctgaatcta aattttaat acaaaagtag ttatatttgt | 120 |
| tgtacattgt aaactataac ttaacttcag tttcagagaa actcatgtgc tcaaaatgta | 180 |
| aaaaagttt cctgttaaat attttgtaaa tgtattgaag acaaaataag aaaaaaaaaa | 240 |
| tataagccac taaatcacac tgtccttggt atcagcaaga gattctgaca taatcagctg | 300 |
| tttttgttta ttactgccat tgaaggccat gtgcattagt cccaagttac acattaaaaa | 360 |
| gtcacatgta gcttaccaac atcagtgctg ttcaagcaca gcctcatcta ctattcaaac | 420 |
| tgtggcacca tctaaaatat gccagaattt ttttattta tgaatttgac cctgaaatat | 480 |
| gtattaatat cactcctgtg attttttgt aatcagctta caattacagg aatgcaagcc | 540 |
| tgattcatta caagtttcac tacactttct ctgacaacat cacctactga actcagacca | 600 |
| gctagttgct ccttaagtat acaatcatgt cactaatcct catttcaatg aaaaataccc | 660 |
| ctattgtact tggtacttgg tagataacca cagagcagta ttatgccatt attgtgaata | 720 |
| caataagagg taaatgacct acagagctgc tgctgctgtt gtgttagatt gtaaacacag | 780 |
| cacaggatca aggaggtgtc catcactatg accaatacta gcactttgca caggctcttt | 840 |
| gaaaggctga aaagagcctt attggcgtta tcacaacaaa atacgcaaat acggaaaaca | 900 |
| acgtattgaa cttcgcaaac aaaaaacagc gattttgatg aaaatcgctt agggatcccc | 960 |
| ccttgctctt caaacaatcc agcttctcct tctttcactc tcaagttgca agaagcaagt | 1020 |
| gtagcaatgt gcacgcgaca gccgggtgtg tgacgctgga ccaatcagag cgcagagctc | 1080 |
| cgaaagttta ccttttatgg ctagagccgg gcatctgccg tcatataaaa gagcgcgccc | 1140 |
| agcgtctcag cctcactttg agctcctcca cacgcagcta gtgcggaata tcatctgcct | 1200 |
| gtaacccatt ctctaaagtc gacaaacccc cccaaaccta aggtgagttg atctttaagc | 1260 |
| tagcttttta catttttcagc tcgcatatat caattcgaac gtttaattag aatgtttaaa | 1320 |
| taaagccaga ttaaatgatt aggctcagtt accggtcttt ttttctcat ttacgtgcga | 1380 |
| actctgctta aactctagtt attctttatt aatatgtggt tattttata tatgtatgtg | 1440 |
| ttatcataac tgtactggct atgtcaggtg gtaatgactg taacgttacg ttactcgttg | 1500 |
| taggcacgac attgaatggg ccggtgttga aataagtctt caaccccttt taacctcaaa | 1560 |
| atgtgctctg gttaacaagg attttaacag ctatcagtat gactgtgcgg ttttaaagcc | 1620 |
| gttagtgagg cacgttgcac acttgatgga tggccggaat gggaagttct ttatgcaggc | 1680 |
| agtgctgcag caggtgtga cctactttag ctaacgttag ccggctaacc agcattcatc | 1740 |
| tgccggtaac ttgagtctaa tattctctca tgtgatatcg aagtgatcaa agacacgtct | 1800 |
| gttagctcac tttaaccaac tgtagtgaaa atagcgcag tgtgcagccc ttcagtcttt | 1860 |
| catttaggct gattattcaa tcattttatt aactattaac gcgttactaa acgtaaggta | 1920 |
| acgtagtcag ttttaataa ctggtgaaaa gtactggttg ggtttaaatg gtgacttata | 1980 |
| attgtgttgg agggggaaac ctttttgata aaggctatat aatctcaaat gaatgggctg | 2040 |
| aggatggtgt tcacaggtgc tttagtgaag tccgctcgtg aagagtcgct gaagtgactg | 2100 |
| cagatctgtg acgcagtcgt tttgggcaga cggccgttga aattcggttg agtaattgat | 2160 |
| accaggtgag gctagaggat gtagaaattc atttgtgtag aatttaggga gtggccctgg | 2220 |
| cgtgatgaat gtcgaaatcc gttcctttt actgaaccct atgtctctgg ctgagtgcca | 2280 |
| caccgccggc agccgcaaag cgtctcaaac cattgccttt tatggtaata atgagaatgc | 2340 |
| agagggactt cctttgtctg gcacatctga ggcgcgcatt gtcacactag cacccactag | 2400 |

```
cggtcagact gcagattgca gcacgaaaca ggaagctgac tccacatggt cacatgctca    2460
ctgaagtgtt gacttccctg acagctgtgc actttctaaa ccggttttct cattcattta    2520
cagttacagc catggcgtat cgatgtcgac tttttttttt tttttttacat ggaataaaat    2580 tttaatttat tctcgttggc tacaggggtt tatcttcatc ctttatgctt ttacactctt    2640
cctcgtcttt tgggaaatct cagttctttc agaggcaaac cttcagcatc cacttcattc    2700
actatgtgta tcggtgaaag ttgttccatt ggagagtctg caggaatgga tagtactgca    2760
tcaccagcat ccatcatcct aaatgttgcc tccacttcac caacgcttct ctttccacca    2820
ggaagccaac catatgacca atgctggcaa agccatgggg gagagcagcc tcagagagag    2880
ctttcgtctt ctggcttgct tcaagaagga catgcacaag gtggaaactt acctgagggt    2940
tgcgaattgc aggagatccc tggattcaaa ctgcaccctg tagatggcgc caatgtattg    3000
ctagccaaag cctgtgacac actttgctgc aaatctaaaa ccagtttaag tcctcaaaat    3060
ctcctaatat aattattatc tggtcttata tatgcaggaa atgtcaacca ggcatggcta    3120
ggtctgttct ctagttccct cccatatcta aacccaacac tattgtattt attcttctca    3180
ttggggagtg ctcgtaaatt aaagacatta agatctgatt taacatttca cagtggtgct    3240
aagcaatata tggcaatata ttttcaaatg tgcccaaatc gctttgactc tagtatttta    3300
tggctccaaa aatggctaaa gatgcctttt gtcgaaactg tcatttggat ggatgggttc    3360
actcccaacc aagtgtatga atgtaaacat ttgtctgtct gatagattat gtccatatta    3420
ttagctcatg ctgttctctt gaagctgtgt gtctttatcc attaaatttc taaactgcat    3480
ccaatgtgtc tgctgtatga cctgtgtggt ttatttttt ctacccgtct caacattaca    3540
cgtaccttac attttcactg ctcggatatt catcaaaatc agtccatatca tccgtccaca    3600 atgaacgagt tcaaaatgga ccgaaaaaaa tgaccagcgg aattc                    3645
```

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 5
cgtccatggc gtatcgatgt cgac                                             24

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 6
agcccatggc tttgccagca ttgg                                             24

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 7

```
aaatgaatgg gctgaggatg                                           20

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 8
tggcttcctg gtggaaaga                                            19

<210> SEQ ID NO 9
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide primer

<400> SEQUENCE: 9
tggcgtgatg aatgtcg                                              17

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 10
ccatggcgta tcgatgtcga c                                         21

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 11
catggctttg ccagcattgg                                           20
```